United States Patent [19]

Grubb et al.

[11] 4,168,146
[45] Sep. 18, 1979

[54] IMMUNOASSAY WITH TEST STRIP HAVING ANTIBODIES BOUND THERETO

[75] Inventors: Anders O. Grubb, Lund; Ulla C. Glad, Malmö, both of Sweden

[73] Assignee: AB Kabi, Stockholm, Sweden

[21] Appl. No.: 649,248

[22] Filed: Jan. 15, 1976

[30] Foreign Application Priority Data

Jan. 27, 1975 [SE] Sweden ................................ 7500841

[51] Int. Cl.² ..................... G01N 33/16; G01N 21/06; G01N 31/14
[52] U.S. Cl. .................................... 23/230 B; 422/56; 424/8; 424/12; 435/7
[58] Field of Search ........................ 23/230 B, 253 T.P; 424/12, 8; 195/103.5 R, 103.5 A; 422/56

[56] References Cited
U.S. PATENT DOCUMENTS

| 3,432,424 | 3/1969  | Zec ........................................ 204/299 |
| 3,645,852 | 2/1972  | Azen ..................................... 424/12 X |
| 3,654,090 | 4/1972  | Schuurs .............................. 195/103.5 R |
| 3,666,421 | 5/1972  | Price .................................... 424/12 X |
| 3,770,383 | 11/1973 | Price .................................... 23/253 TP |
| 3,789,116 | 1/1974  | Kay ...................................... 424/12 X |
| 3,790,663 | 2/1974  | Garrison ................................. 424/12 |
| 3,791,933 | 2/1974  | Moyer .................................. 23/253 TP |
| 3,843,450 | 10/1974 | Saxholm ............................... 23/230 B |
| 3,859,430 | 1/1975  | Parikh .................................. 424/12 X |
| 3,868,219 | 2/1975  | Hurenkamp ....................... 424/12 X |
| 3,876,504 | 4/1975  | Koffler ................................. 424/12 X |
| 4,036,946 | 7/1977  | Kleinerman .................... 23/230 B X |

Primary Examiner—Sidney Marantz
Attorney, Agent, or Firm—A. A. Orlinger

[57] ABSTRACT

A test strip for carrying out immunoassays. The test strip is a bibulous carrier to which antibodies are bound. The immunoassay is carried out by wetting the test strip with the aqueous solution containing a suspected antigen. The test strip is then contacted with an aqueous solution containing labeled antibodies.

9 Claims, No Drawings

IMMUNOASSAY WITH TEST STRIP HAVING ANTIBODIES BOUND THERETO

This invention is that of (a) a diagnostic device for immunochemical quantification, preferably prepared as a test strip, and comprising a porous (in the sense of capillarity-possessing) carrier material, as well as (b) the method of conducting such assay by use of this diagnostic device.

More specifically, the diagnostic device comprises such capillarity-possessing porous carrier material with antibody bound to it. The assay method comprises immunochemical quantification characterized by the utilization of the capillarity of the porous carrier material to which antibodies are bound in a way known to the art as, for instance, by adsorption or absorption or covalent binding such as by use of (i) a cyanogen halide such as cyanogen bromide or (ii) glutaraldehyde.

In use, generally the capillarity-possessing diagnostic device is immersed in the sample containing an antigen to be quantified. A capillary migration then takes place. Thereafter the antigen-containing areas of the diagnostic device are indicated by the addition (to the sample-wetted device) of antibodies bound to a suitable color indicator such as a fluorescent compound or an enzyme that catalyzes a color reaction.

Antibodies suitable for use in this invention are obtained by techniques known to the art by immunizing an animal of a species different from the species bearing the antigen of interest to determine. For instance, antibodies against human proteins (albumin, gammaglobulin, fibrinogen, and transferrin) e.g. are readily obtained from the rabbit, goat, sheep, horse and guinea pig. Such antibodies are present in the blood of immunized individuals; more specifically the gammaglobulin (immunoglobulin) fraction contains the antibodies.

The hitherto used quantitative immunochemical methods are based on immunodiffusion as, for instance, the Mancini or Ouchterlony methods named after their respective inventors, or on immunoelectrophoresis as in Laurell's electroimmunoassay. These methods, as well as their variants, bring about the necessary interaction between antigen and antibody by a diffusion process and/or an electrophoretic process. On the other hand, the method of this invention is based on utilizing the capillary force of a porous carrier material device (of the invention) having antibodies bound to it.

Porous capillarity-possessing materials suitable for use in the invention are, for example, various kinds of cellulose fibre-containing materials such as filter paper, chromatographic paper, ion exchange paper, a cellulose acetate film, cellulose acetate discs, cellulose thin-layer chromatography discs, as well as films or such materials as starch, as SEPHADEX which is a 3-dimensional network or matrix of dextran chains cross-linked with epichlorhydrin (product of Pharmacia Fine Chemicals, Uppsala, Sweden and Piscatawny, N.J.), films of plastic material such as polyvinylchloride, ceramic material, and of combinations such as polyvinylchloride-silica.

The invention is illustrated by, but not restricted to, the following examples:

PRODUCTION OF THE DIAGNOSTIC DEVICES:

EXAMPLE 1

Binding of antibodies on capillarity-possessing material with CNBr 10 g. of filter paper as the cellulose-containing material are immersed in distilled water for 5 minutes. Thereafter, a solution of 8 g. of CNBr in 300 ml. of distilled water is admixed and the pH is adjusted to 10.5 with 1 M NaOH and maintained at this level by suitable addition of any of the needed pH adjustment agents. The reaction is continued over a period of 20 minutes and then the supernatant solution is decanted. The CNBr-treated cellulose material is washed with 2 l. of 0.005 M $NaHCO_3$. After removal of the washing solution, the CNBr-treated cellulose material is incubated over night at $+4°$ C. in a solution of 500 mg. of rabbit gammaglobulin against human gammaglobulin (IgG Fc fragment) in 10 ml. of 0.1 M $NaHCO_3$ and then incubated again for 3 hours with 100 ml. of 0.005 M ethanolamine aqueous solution, followed by another washing with 500 ml. of 0.5 M $NaHCO_3$, and then 200 ml. of 0.1 M acetate buffer having pH 4.0 and 500 ml. of 0.075 M sodium barbiturate buffer with 0.3% albumin added at $+4°$ C.

EXAMPLE 2

Binding of antibodies on capillarity-possessing material with glutaraldehyde 0.6 g. of cellulose acetate film is incubated with a solution of 100 mg. of rabbit gammaglobulin against human gammaglobulin (IgG Fc fragment) in 10 ml. of 0.1 M phosphate buffer having a pH of 6.8 for 30 minutes. When the solution has been decanted, the film is incubated in 10 ml. of 1% glutaraldehyde aqueous solution during 30 minutes, followed by incubation in 10 ml. of 1.0 M aqueous methylamine for 15 minutes. Thereafter, the film is washed with 100 ml. of 0.075 M sodium barbiturate buffer and kept in the same buffer at $+4°$ C. to which has been added 0.3% albumin.

EXAMPLE 3

Binding of antibodies on capillarity possessing carrier material by adsorption or absorption 10 g. of polyvinylchloride-silica (Microporous Plastic Sheet, silica content about 50%, product of Amerace Esna Corporation, New York, N.Y.) are incubated over night at $+4°$ C. with a solution of 500 mg. of rabbit gammaglobulin against human gammaglobulin (IgG Fc fragment) in 100 ml. of 0.1 M phosphate buffer at pH 6.8. After completion of this incubation, the material is washed with 1 liter of phosphate-buffered physiological NaCl at pH 7.0. The resulting polyvinylchloride-silica sheet with adsorbed gammaglobulin is dried between filter papers.

EXAMPLE 4

Preparation of fluorescent antibody conjugates:

(a) 720 mg. of rabbit gammaglobulin against human gammaglobulin (IgG Fc fragment), 0.57 g. of NaCl, 0.259 g. of $NaHCO_3$ and 0.049 g. of $Na_2CO_3 . 10 H_2O$ are dissolved in 72 ml. of distilled water. The resulting reagent solution is cooled in an icebath, and 36 mg. of fluoresceinisothiocyanate are added while stirring. The solution is then left in the cool while stirring for 18 hours. Thereafter, the mixture is dialyzed against phosphate buffered physiological NaCl at a pH of 7.0 till the dialyzing fluid stops fluorescing. The resulting antibody conjugate is frozen.

(b) 720 mg. of rabbit gammaglobulin against human gammaglobulin (IgG Fc fragment), 0.57 g of NaCl, 0.259 g. of $NaHCO_3$ and 0.049 g. of $Na_2CO_3 . 10 H_2O$ are dissolved in 72 ml. of distilled water. The resulting reagent solution is cooled in an icebath, and 9 mg. of rhodamine dissolved in 2 ml. of acetone are added while stirring. The solution is left in the cool while stirring for 18 hours. Thereafter, the mixture is dialyzed against phosphate buffered physiological NaCl at pH 7.0 till the dialyzing fluid stops fluorescing. The resulting antibody conjugate is frozen.

(c) 720 mg. of rabbit gammaglobulin against human gammaglobulin (IgG Fc fragment), 0.57 g. NaCl, 0.259 g. $NaHCO_3$ and 0.049 g. of $Na_2CO_3. 10 H_2O$ are dissolved in 72 ml. of distilled water. The resulting reagent solution is cooled in an icebath, and 20 mg. of dansyl chloride dissolved in 7 ml. of acetone are added while stirring. The solution is left in the cool while stirring for 18 hours. Thereafter, the mixture is dialyzed against phosphate buffered physiological NaCl at a pH of 7.0 till the dialyzing fluid stops fluorescing. The resulting antibody conjugate is frozen.

EXAMPLE 5

Preparation of LDH isoenzyme $H_4$ antibody conjugate

A suspension of 4.5 mg. of LDH (lactic dehydrogenase) isoenzyme $H_4$ in ammonium sulfate is dialyzed against 0.1 M phosphate buffer at pH 6.8. While stirring, 2.25 mg. of rabbit gammaglobulin against human gammaglobulin (IgG Fc fragment) are added and phosphate buffer to make a total volume of 1.35 ml. When all of the rabbit gammaglobulin has dissolved, 45 μl of 1% glutaraldehyde solution is added dropwise, and the reaction is left to stand in room temperature for 2 hours. The mixture is then dialyzed against sodium barbiturate buffer and the conjugate stored at +4° C. Before use, it is diluted with 10 ml. of barbiturate buffer to which 2% albumin has been added.

EXAMPLE 6

Checking of antibody binding to carrier

Two strips of any one of these porous materials treated with antibodies in accordance with any of the preceding examples 1 to 3, and two untreated strips of the same porous materials are used for the test. One strip of each kind (i.e. treated and untreated) is incubated in a solution of 1 mg. of human gammaglobulin (IgG) per ml. of sodium barbiturate buffer. All strips are then washed with 20 ml. of sodium barbiturate buffer containing 0.15 M NaCl, ten times in all, whereafter they are incubated in a solution of fluoresceinisothiocyanate antibody conjugate for 10 minutes. After repeated washings as in the foregoing step, the strips are dried and inspected in ultraviolet light at a wavelength of 340 nm, to establish that fluorescence is present only in the strips that contain the bound antibodies and that have been incubated in the IgG-solution. When checking on strips prepared according to Example 3, strips treated with bovine albumin are used as controls.

IMMUNO-CHEMICAL QUANTIFICATION

EXAMPLE A

Diagnostic devices produced in accordance with the present invention are used for immuno-chemical quantification for diagnostic purposes in the following way:

The material to be tested (i.e. quantified) is placed—in a known quantity, preferably between 1 μl and 3 μl—on a selected device form of the capillarity possessing carrier material of this invention at the same time as equal volume quantities of a standard solution having a known content of the antigen to be tested and in various dilutions are placed next to the test solution.

0.075 M sodium barbiturate buffer with an additive of 0.3% albumin can, for example, be used as a mobile phase to facilitate capillary migration.

The capillary migration can be performed in both open and closed test recipients; further, the mobile phase can be made to move upwards and downwards. Beneficially, the combination of a closed recipient and rising mobile phase should be employed. At an optional time, from about 10 to about 45 minutes, after initiation of the capillary migration, the moist carrier material is transferred to an antibody solution containing either fluoresceinisothiocyanate- or an enzyme that catalyzes a color-developing reaction bound antibodies such as lactic dehydrogenase (LDH)-bound antibodies. The preferable incubation time for either of these indicator solutions is 10 minutes. After incubation, the carrier material is washed under running water at +37° C. for 5 minutes, followed by incubation for preferably 2×5 minutes in 20 ml. of sodium barbiturate buffer, containing 0.2% albumin and 0.15 M NaCl.

The extent that fluorescent antibodies are used for the identification of the migration distance of the antibody is measured in ultraviolet light at 340 nm. If LDH antibody solution is used, the carrier material is treated in a dye bath composed as follows:

30 mg. of nitroblue tetrazolium (Sigma: 2,2′-di-p-nitrophenyl-5,5′-di-phenyl-3,3′-(3,3-dimethoxy-4,4′-diphenylene)-ditetrazolium chloride) and 40 mg. of NAD are dissolved in 56 ml. of 0.05 M TRIS buffer at pH 7.4. To the mixture are added 1.60 ml. of 3.6 M lithium lactate, 5 ml. of 0.06 M calcium cyanide, and a few grains of methylphenazonium metasulfate dissolved in 2 ml. of distilled water. The capillary containing material is incubated in the dye bath at +37° C. until a distinct coloring can be observed. The color development is due to the fact that the LDH catalyzes the reaction of lactate+NAD⇌pyruvate+$NADH_2$ and that $NADH_2$ quantitatively reduces the nitroblue tetrazolium to an insoluble lilac-colored formazan type compound (Organic Chemistry, Fieser & Fieser, Reinhold Publishing Corporation, New York, 1956).

The indicated, antigen-covered areas of the diagnostic device will then increase in magnitude with the increasing content of antigen of the tested samples. The bound antibody molecules retard the migration of the antigen molecules by exchange reactions during the capillary migration. The higher the concentration of antigens, the less the retarding effect because the average time of an antigen molecule remaining bound to an antibody will decrease with an increasing concentration of antigens.

EXAMPLE B

Strips of the antibody-containing, porous (i.e. having capillaries) carrier material prepared in accordance with this invention are immersed to a determined depth of, for instance, 3 mm. in a small volume of a solution of the antigen material to be tested. The thus initiated capillary migration is allowed to continue for from about 3 to about 20 minutes and then interrupted by removing the strip from the solution. The migration distance of the antigen is then measured as described in Example A, and the result is evaluated according to Example A.

The diagnostic test device of the invention advantageously is prepared in the form of a test strip composed of the porous (i.e. capillary-possessing) carrier material. The term "strip" is intended broadly to embrace the diagnostic device whether it be made of filter paper thickness, or of slightly greater thickness if need be, or in the form of a film (which also may be a membrane or a layer) or as discs; all as exemplified on page 2 above, or as a relatively similarly thin flat stick or small diameter rod.

In the expression "carrier material", the term "carrier" is used in the sense that there is bound to that carrier material the antibodies, as referred to in the second paragraph of this disclosure, for example, by adsorption or by so-called covalent binding in the form of a test strip which comprises porous capillarity-possessing antibody carrier material to which the antibodies are bound.

The microporous plastic sheet of polyvinyl chloride modified by having finely divided silica substantially uniformly interspersed throughout the porous polymer matrix of Example 3 can be replaced by a similar sheet of a likewise suitably permeable or porous, continuous polymeric matrix of the commonly available vinyl chloride-propylene copolymer, or vinyl chloride-vinyl acetate copolymer, in each of which the finely divided silica similarly is embedded.

Thus, to avoid making this specification prolix, Example 3 should be considered as repeated twice as if written out in full in one case with its microporous plastic sheet replaced by the corresponding silica-modified vinyl chloride-propylene copolymer microporous plastic sheet and in the other case replaced by the corresponding silica-modified vinyl-chloride-vinyl acetate copolymer microporous plastic sheet.

The foregoing microporous sheets are available with mean pore diameter of from 0.1 to about 1 micron and above, for example, 0.1, 0.2, 0.3 and 0.5 micron in diameter, and with total porosity measuring (by mercury intrusion) from about 1.1 to about 1.8 milliliters per gram of the silica-modified microporous plastic material.

While the invention has been explained more fully by detailed description of certain specific embodiments of it, it is understood that various modifications and substitutions may be made in them within the scope of the appended claims which are intended to cover also equivalents of the specific embodiments.

What is claimed is:

1. In a method of immunochemical quantification, the improvement which comprises wetting a diagnostic test strip consisting essentially of a porous, capillarity-possessing carrier material having antibodies covalently bound to it, with an aqueous sample containing the antigen to be quantified, allowing the capillary migration to take place, and then assaying the antigen-containing area of said diagnostic test strip by wetting it with antibodies in an aqueous vehicle, said antibodies being bound to a water-soluble fluorescent color indicating compound or to an enzyme that catalyzes a color-developing reaction.

2. The method as claimed in claim 1, wherein the antibodies in the aqueous vehicle are bound to an enzyme that catalyzes a color-developing reaction.

3. The method as claimed in claim 2, wherein the enzyme is lactic dehydrogenase.

4. The method as claimed in claim 1, wherein the antibodies in the aqueous vehicle are bound to a water-soluble fluorescent color indicating compound.

5. The method improvement as claimed in claim 4, wherein the diagnostic test strip is composed of a polyvinyl chloride-silica combination onto which have been adsorbed antibodies against human gammaglobulin.

6. The method improvement as claimed in claim 4, wherein the color indicator compound is fluoresceinisothiocyanate, rhodamine, or dansyl chloride.

7. The method improvement as claimed in claim 6, wherein the antibody-bound color indicator is fluoresceinisothiocyanate.

8. A diagnostic test device useful for immunochemical quantification, which is substantially a carrier strip comprising a silica-modified micro-porous polymer having finely divided silica substantially uniformly embedded in a permeable, continuous polymeric matrix selected from the group consisting of polyvinyl chloride, vinyl chloride-propylene copolymer, and vinyl chloride vinyl acetate copolymer, said strip having antibodies bound to it.

9. The diagnostic test device as claimed in claim 8, wherein the carrier material is a porous polyvinyl chloride matrix.

* * * * *

UNITED STATES PATENT AND TRADEMARK OFFICE
CERTIFICATE OF CORRECTION

PATENT NO. : 4,168,146
DATED : September 18, 1979
INVENTOR(S) : Anders O. Grubb and Ulla C. Glad It is certified that error appears in the above-identified patent and that said Letters Patent are hereby corrected as shown below:

Column 1 line 35, after the opening parenthesis insert "e.g.".

Column 1 line 36, delete "e.g.".

Column 2 line 64 "$Na_2CO_3 \cdot 10 H_2O$" should read -- $Na_2CO_3 \cdot 10 H_2O$ --

Column 3 line 7, "$Na_2CO_3 \cdot 10 H_2O$" should read -- $Na_2CO_3 \cdot 10 H_2O$ --.

Column 3 line 19 (but actually line 18), "$Na_2CO_3 \cdot 10 H_2O$" should read -- $Na_2CO_3 \cdot 10 H_2O$ --.

Signed and Sealed this

Eighth Day of July 1980

[SEAL]

Attest:

SIDNEY A. DIAMOND

Attesting Officer

Commissioner of Patents and Trademarks